United States Patent
Blohm et al.

(10) Patent No.: US 7,684,542 B2
(45) Date of Patent: Mar. 23, 2010

(54) METHOD FOR GENERATING AN IMAGE SEQUENCE FOR A 3D RECONSTRUCTION

(75) Inventors: Lutz Blohm, Erlangen (DE); Thomas Brunner, Nürnberg (DE); Holger Kunze, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/283,404

(22) Filed: Sep. 11, 2008

(65) Prior Publication Data

US 2009/0074135 A1     Mar. 19, 2009

(30) Foreign Application Priority Data

Sep. 17, 2007   (DE)   ........................ 10 2007 044 368

(51) Int. Cl.
*G01N 23/04*     (2006.01)

(52) U.S. Cl. ........................................................ 378/62
(58) Field of Classification Search ............... 378/4–20, 378/62, 193–198, 901; 382/131, 132
See application file for complete search history.

(56) References Cited

FOREIGN PATENT DOCUMENTS

| DE | 10 2005 023 165 A1 | 11/2006 |
|---|---|---|
| DE | 10 2006 037 564 B3 | 3/2008 |

*Primary Examiner*—Courtney Thomas

(57) ABSTRACT

When recording an image sequence, it is possible to deviate from passing through a perfect curve path. There is described how an alternative curve path can be determined. An envelope is determined, a point is determined, which is the center point of the region of interest and then the detector is moved such that it is at right angles in each instance to a line which emanates from the point and simultaneously touches the envelope tangentially. As a result, the region of interest is mapped as optimally as possible in the image sequence so that as good a 3D reconstruction as possible can be obtained.

9 Claims, 2 Drawing Sheets

METHOD FOR GENERATING AN IMAGE SEQUENCE FOR A 3D RECONSTRUCTION

CROSS REFERENCE TO RELATED APPLICATIONS

This application claims priority of German application No. 10 2007 044 368.6 DE filed Sep. 17, 2007, which is incorporated by reference herein in its entirety.

FIELD OF INVENTION

The invention relates to a method for generating an image sequence for a 3D reconstruction by means of an x-ray image recording system, which includes an x-ray C-arm which supports an x-ray source and a flat panel detector.

BACKGROUND OF INVENTION

A 3D reconstruction of a mapped region of an object, in particular of a patient, can then be derived if mappings are recorded from different directions. The 3D reconstruction in turn allows cross-sectional images to be calculated. To record the object from different directions, an x-ray C-arm is conventionally moved at equal angular distances through an angle of 180°. With the positions defined by the angular distances, an x-ray image (a so-called projection) is recorded in each instance.

To ensure that a region of interest of the object can actually be reconstructed, it is necessary for this region to be completely mapped in each of the recorded x-ray images. This is then problematical if the region of interest is located beyond the center point of the object, which usually forms the rotation center. This is the case for instance if the liver of a patient is to be mapped. The region of interest, which lies outside the center point of the patient, can not define a new center point for a circular movement, because otherwise the x-ray source or the x-ray detector would knock against the patient.

SUMMARY OF INVENTION

DE 10 2006 037 564.5, which was published after the date of filing of the present application, describes moving an x-ray C-arm precisely on a circular path when an image sequence is generated. Instead, the C-arm is tracked in a collision-free fashion in synchrony with the rotation such that the object region of interest, at least with each rotation angle, with which an image recording takes place, lies within a cone of rays of an x-ray beam bundle of the x-ray recording system. This movement of the x-ray C-arm which deviates from a circularity is particularly enabled in the case of modern x-ray image recording systems, for instance with such a system, with which the x-ray C-arm is arranged on the hand of a 6-axis articulated arm robot.

DE 10 2006 037 564.5 does not detail how the x-ray C-arm can be tracked.

It is an object of the present invention to further develop the method known from DE 10 2006 037 564.5 and to provide a special instruction as to how an x-ray C-arm can be moved so that an optimum 3D reconstruction can be achieved.

The object is achieved by a method with the steps according to an independent claim and an x-ray image recording system with the features according to a further independent claim.

The method for generating an image sequence thus includes the following steps:

a) Receiving, by means of the image recording system, an entry to determine a (closed) envelope in (fixed) coordinates which are defined at the x-ray image recording system,
b) Receiving, by means of the image recording system, an entry to determine a point in a region of interest (inside the envelope),
c) Calculating a plurality of positions of the x-ray C-arm, with which the flat panel detector is on the one hand arranged at right angles to a straight line which emanates from the point in the region of interest and on the other hand touches the envelope tangentially,
d) Passing through the positions calculated in step c) by moving the x-ray C-arm and automatically recording an x-ray image with each position in each instance.

Such an envelope which, with the usual position of the patient in the x-ray recording system, surrounds the patient in any case, is entered in a suitable fashion. The envelope can consist of two half ellipses, the parameters of which are entered numerically or which are interactively drawn on a monitor by the person carrying out the entering. The envelope determines the extent to which the flat panel detector is able to move. If the envelope surrounds the patient, the fact that the flat panel detector tangentially touches the envelope means that the flat panel detector does not touch the patient. As a result, the objective of preventing the flat panel detector from colliding with the patient is achieved.

Also with the method, attempts are essentially made to rotate the x-ray C-arm in rotational positions through a range of 180°, or in rougher terms 160° to 200°. The method allows the point in the region of interest to be the actual center of rotation, because the flat panel detector is at right angles to a straight line which emanates from the point in the region of interest in each instance. The different straight lines move apart by means of rotation. Only the distance of the flat panel detector from the point in the region of interest must be adjusted such that this tangentially touches the envelope.

Reference is incidentally made to the term tangentially touching the envelope by the flat panel detector meaning that the graphically illustrated flat panel detector tangentially touches the envelope, because the real flat panel detector is not able to.

Within the scope of the inventive method, it is possible to choose between a high resolution of the region of interest and a representation of as large a part of a region of interest in the images as possible. The angular range of 360° can be divided into two sub regions, one of which is to be precisely selected such that the flat panel detector lies as close as possible in each instance to the point in the region of interest and this sub region is crossed if a high resolution is desired. The other sub region is naturally determined such that the flat panel detector is distanced as far as possible from the point in the region of interest and this sub region is crossed if the desire is to illustrate as large a part of the region of interest as possible. The x-ray image recording system receives a corresponding entry with this preferred embodiment, by means of which a choice is made between the two possibilities "large resolution" and "representation of a large region".

It will naturally be difficult to determine the point in the region of interest without referring to any x-ray image. A preferred embodiment, which includes step b) is thus such that the x-ray image recording system receives an entry for determining an image recording position of the x-ray C-arm and for recording an x-ray image in this image recording position at least once (preferably twice) and then receives an entry for determining a point in the recorded x-ray image. In particular, if the x-ray C-arm is moved into positions which are perpendicular to one another, in which positions an x-ray image is recorded in each instance, the region of interest can be particularly well identified by a doctor and an individual point can be well-defined.

The x-ray image recording system includes an x-ray C-arm, which supports an x-ray source and a flat panel detector and a control unit, and this control unit is designed to:
a) receive a first entry and to determine an envelope in coordinates defined at the x-ray image recording system on the basis of this first entry,
b) receive a second entry and to determine a point in the coordinates defined at the x-ray image recording system on the basis of this second entry,
c) calculate a plurality of positions of the x-ray C-arm, wherein the flat panel detector (and/or its graphical representation) is at right angles on the one hand to a straight line which emanates from the point in the region of interest and on the other hand touches the envelope tangentially,
d) actuate control elements, which move the x-ray C-arm such that the positions are passed through one after the other, with the control unit providing for the recording of an x-ray image in each instance.

As already mentioned in the introduction, the x-ray image recording system preferably includes a 6-axis articulated arm robot, at the hand of which the x-ray C-arm is supported.

There should again also be a choice between the option as to whether a high resolution is to be achieved or whether as large a volume as possible is to be reconstructed. To this end, the x-ray image recording system allows a third entry, with the control unit selecting the plurality of positions such that the flat panel detector lies as close as possible to the point for a high resolution and the flat panel detector is distanced as far as possible from the point for a large volume.

BRIEF DESCRIPTION OF THE DRAWINGS

A preferred embodiment of the invention is described below with reference to the drawings, with FIG. 1 illustrating the problem underlying the invention when recording an image sequence according to the prior art on a schematic drawing, FIG. 2 likewise following on from FIG. 1 illustrating the underlying problem on the one hand and on the other hand the solution to overcome the problem according to the invention, FIG. 3 schematically illustrating the discrepancy between a good resolution and the reconstruction of as large a volume as possible, FIG. 4 schematically illustrating the preferred position of the x-ray image recording system with preference for one of the two said options.

DETAILED DESCRIPTION OF INVENTION

Figure 1:
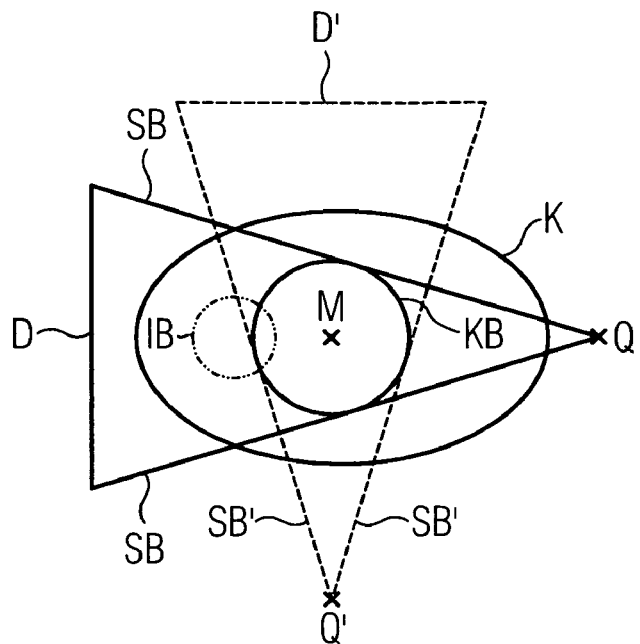

FIG. 1 shows a symbolic body K. Mappings of the body K are to be obtained with the aid of an x-ray image recording system, with FIG. 1 symbolically illustrating an x-ray source Q and an x-ray detector D. A beam bundle SB moves from the x-ray source Q to the detector D. The x-ray source Q and the detector D are affixed to an x-ray C-arm, which for reasons of simplicity are not shown in FIG. 1. The x-ray C-arm is rotated about the center point M of the body K so that the source Q reaches the position Q' and the detector D reaches the position D'. The beam bundle SB' then passes through the body K. As a result of x-ray images (projections) recorded in the respective positions, parts of the body K can be reconstructed. A three-dimensional reconstruction composed of a plurality of x-ray images, which were recorded in each instance after rotating the source Q and the detector D, is only possible of the region which is mapped in all x-ray images. This is the circular region KB drawn in FIG. 1. It is now such that a region of interest IB lies beyond the center point M and this barely intersects the circular region KB. The region of interest IB can thus not be represented by the 3D reconstruction.

Figure 2:
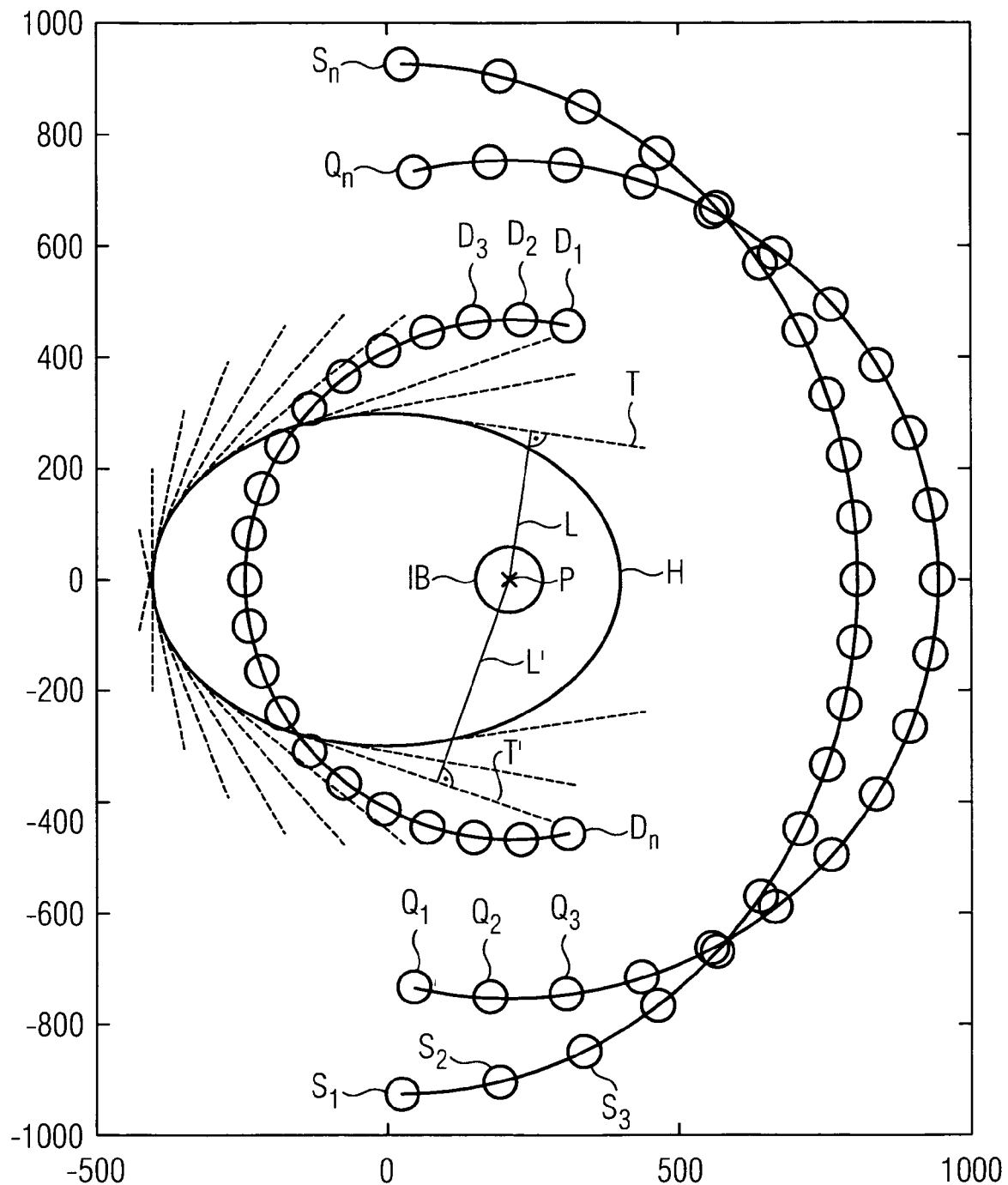

Instead of rotating the x-ray C-arm about the center point M of the body K, it would now be appropriate to determine the center point P of the region of interest IB and to rotate about this. FIG. 2 nevertheless illustrates that this is associated with difficulties: if the x-ray C-arm was rotated such that it rotates precisely on one circular path about the center point P of the region of interest IB, such that the x-ray source passes through the positions $Q_1, Q_2, Q_3$ etc. to $Q_n$, the detector would have to pass through the positions $D_1, D_2, D_3$ etc. to $D_n$ and would as a result collide with the body.

It is now desirable, within the meaning of as good a reconstruction of the region of interest IB as possible, to move the x-ray source and the x-ray detector such that a rotation about the point P is almost achieved. This takes place by means of the following measures: an envelope H is defined, which in any case surrounds the body K and is at present elliptical. In a complicated version, the envelope H can consist of two half ellipses, with one surrounding the back of the patient and the other the ribcage. During the definition of the envelope H, he/she orientates him/herself to the standard position of the patient on the patient couch of the x-ray image recording system. It should be noted that the envelope H in FIG. 2 does not appear any different to the patient contour K in FIG. 1. The patient contour K is however a schematic representation, while the envelope H can actually take the shape shown in FIG. 2. The precise shape of the envelope can be programmed into the image recording system, i.e. the same is entered during the recording of the operation or an entry of the envelope H can take place interactively by means of a user so that this can respond to individual properties of the respective patient. For instance, the envelope H can be smaller if the patient is slim and must be bigger if the patient is corpulent. The region of interest IB is determined by way of its center point P. To this end, two x-ray images are recorded in advance, between which the x-ray source and x-ray detector are moved about 90° respectively. The treating doctor can interactively mark a point in both x-ray images by way of an entry apparatus, for instance a computer mouse. These points represent lines and the x-ray image recording system can calculate the cross-sectional point of these lines and this cross-sectional point then corresponds to the point P.

Positions of the detector are now calculated as follows: starting from the point P, a straight line L is drawn in a certain direction. That tangent T, which is precisely at right angles to the line L, is now sought for the envelope H. This tangent then defines the detector position: the detector is subsequently to be moved such that an image of the detector coincides with the tangent T. Such a tangent T and/or T' is now determined for different lines L and L' in each instance and a sequence of tangents, which correspond in each instance to detector positions, results herefrom. Assigned to the tangents T to T', a sequence of positions $S_1, S_2, S_3$ etc. to $S_n$ is produced, through which the x-ray source passes. After such positions were calculated for the x-ray detector (tangents T and/or T') and appropriately for the x-ray source ($S_1$ to $S_n$), the positions are passed through one after the other. As can be seen by comparison with the positions $Q_1$ to $Q_n$ in FIG. 2, the positions $S_1$ to $S_n$ also correspond to a rotation about the point P, with a displacement additionally taking place such that the detector touches the envelope H in each instance. If the envelope H is defined such that the patient is located inside the envelope, this means that the detector never collides with the patient and collides less than ever with the x-ray source.

Figure 3:
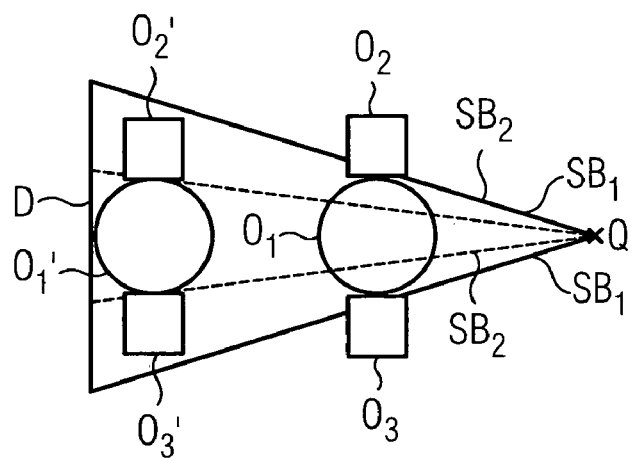

A selection can now be made to determine whether a high resolution is desired or whether the largest possible volume of the region of interest IB is to be mapped. How these requirements eliminate each other mutually is described in FIG. 3: An object consists of the object parts $O_1$, $O_2$ und $O_3$. If the object is relatively close to the source Q, the beam bundle $SB_1$, which reaches the detector D, only passes through the object part $O_1$. Only this object part $O_1$ is thus mapped. As the object part $O_1$ is however relatively close to the source Q, a relatively good resolution is achieved within the object part $O_1$. When moving the object in the direction of the detector, the entire beam bundle $SB_1$ by contrast passes through all three object parts $O_1'$, $O_2'$ and $O_3'$. As only one part of the beam bundle $SB_1$, the beam bundle $SB_2$, passes through the object part $O_1'$, this is resolved in a poorer manner than with the other position. It thus applies: the closer the object to the detector D, the larger the resolved volume and the poorer the resolution.

Figure 4:
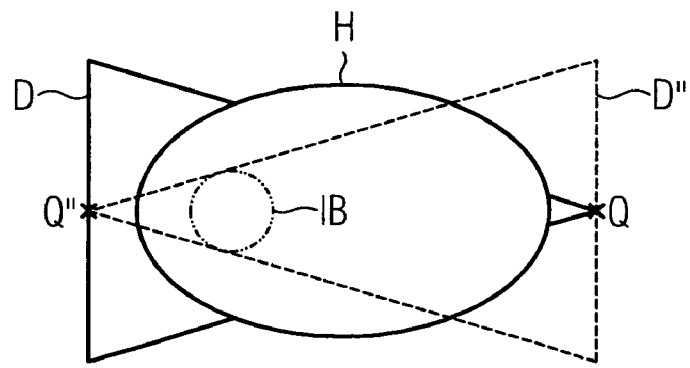

If one wishes to map the region of interest IB in the envelope H, the selection possibility shown in FIG. 4 exists: Either the source Q is positioned at a distance from the region of interest IB and the detector D is positioned close to the region of interest, or the arrangement is rotated about 180° and the source Q" is positioned close to the region of interest and the detector D" is positioned at a distance from the region of interest. The positions $S_1$, $S_2$, $S_3$ to $S_n$ of the x-ray source in FIG. 2 correspond to the situation with the source Q" and the detector D" from FIG. 4. This means that with the positions from FIG. 2, priority is given to mapping a larger volume. Positions can however be completed with positions (not shown in FIG. 2), if tangents are selected in respect of the envelope H, which are at right angles to lines which extend with one portion toward the right side in FIG. 2. The positions $S_1$ to $S_n$ can thus be completed with complementary positions and a quasi rotation through 180° about the point P can likewise be defined, with which the detector is located in each instance particularly close to the region of interest IB.

With the x-ray image recording system, which is to pass through the positions for recording a sequence of x-ray images, a selection can be made with a preferred embodiment as to whether a higher resolution is desired or whether a higher volume of the region of interest is instead to be mapped and a sequence of suitable positions is accordingly selected, namely either the sequence of positions $S_1$ to $S_n$ for the x-ray source or a sequence which is complementary to this sequence.

With the following invention, only the recording of the image sequence for the 3D reconstruction is of interest and not the 3D reconstruction itself. Methods were already developed in the prior art to determine how such 3D reconstructions can be recorded on the basis of projections, which were not recorded with positions which correspond to the positions $Q_1$ to $Q_n$ and $D_1$ to $D_n$ in FIG. 2, whereby no movement along a circular path was made. Details pertaining hereto can be inferred from DE 10 2006 037 564.5.

The method allows an optimum mapping of the region of interest IB in the image sequence, so that the 3D reconstruction particularly effectively allows the representation of sectional images through the region of interest.

The invention claimed is:

1. A method for generating an image sequence for a 3D reconstruction by means of an x-ray image recording system with an x-ray C-arm, comprising:

providing an x-ray source and an x-ray detector supported by the C-arm;

receiving an entry for determining an envelope in coordinates defined at the x-ray image recording system;

receiving an entry for determining a point in a region of interest;

calculating a plurality of positions of the x-ray C-arm, wherein the flat panel detector is at right angles in each instance to a straight line which emanates from the point in the region of interest and touches the envelope tangentially;

passing through the positions calculated by moving the x-ray C-arm; and automatically recording an x-ray image with each position respectively.

2. The method as claimed in claim 1, wherein such a plurality of positions is calculated such that the straight lines, on which the flat panel detector rests in each instance, move away from one another by rotating through a range of 160° to 200° about the point in the region of interest.

3. The method as claimed in claim 2, wherein prior to the calculation of the plurality of positions an entry is received, by means of which a selection is made between two possibilities, the range of 160° to 200°, with the selection of the first possibility thus being determined such that the flat panel detector lies as close as possible to the point in the region of interest and with the selection of the second possibility, wherein it is thus determined that the flat panel detector is moved as far away from the point of the region of interest as possible.

4. The method as claimed in claim 2, wherein prior to the calculation of the plurality of positions an entry is received, by means of which a selection is made between two possibilities and the range of 160° to 180°, with the selection of the first possibility thus being determined such that the flat panel detector lies as close as possible to the point in the region of interest and with the selection of the second possibility, wherein it is thus determined that the flat panel detector is moved as far away from the point of the region of interest as possible.

5. The method as claimed in claim 2, wherein prior to the calculation of the plurality of positions an entry is received, by means of which a selection is made between two possibilities and the range of 180°, with the selection of the first possibility thus being determined such that the flat panel detector lies as close as possible to the point in the region of interest and with the selection of the second possibility, wherein it is thus determined that the flat panel detector is moved as far away from the point of the region of interest as possible.

6. The method as claimed in claim 1, wherein the x-ray image recording system receives at least once an entry for determining an image recording position of the x-ray C-arm and for recording an x-ray image in this image recording position and then receives an entry for determining a point in the recorded x-ray image.

7. The method as claimed in claim 6, wherein the x-ray image recording system receives at least once an entry for determining an image recording position of the x-ray C-arm and for recording an x-ray image in this image recording position and then receives an entry for determining a point in the recorded x-ray image, when receiving also the entry for determining an envelope in coordinates defined at the x-ray image recording system.

8. An x-ray image recording system with an x-ray C-arm, comprising:

an x-ray source and a flat panel detector supported by the C-arm; and a control unit, to:

receive a first entry and to determine an envelope in coordinates defined at the x-ray image recording system on the basis of this first entry, receive a second entry and to determine a point in the coordinates defined at the x-ray image recording system on the basis of this second entry, calculate a plurality of positions of the x-ray C-arm, wherein the flat panel detector is in each instance arranged at right angles to a straight line which emanates from the point in the region of interest and touches the envelope tangentially, actuate control elements for the x-ray C-arm such that the positions are passed through one after the other in order to record an x-ray image in each instance.

9. The x-ray image recording system as claimed in claim 8, wherein the x-ray image recording system allows a third entry, which determines whether a high resolution is to be achieved or as large a volume as possible is to be reconstructed, with the control unit selecting the plurality of positions such that for a high resolution the flat panel detector lies as close as possible to the point in the region of interest and for a large volume, the flat panel detector lies as far as possible from the point in the region of interest.

* * * * *